United States Patent
DeToro et al.

(10) Patent No.: US 7,011,641 B1
(45) Date of Patent: Mar. 14, 2006

(54) KNEE BRACE IMMOBILIZER

(75) Inventors: William DeToro, Poland, OH (US);
Brian Perala, Geneva, OH (US);
Robert Lin, Weathersfield, CT (US)

(73) Assignee: Anatomical Concepts, Inc., Poland, OH (US)

( * ) Notice: Subject to any disclaimer, the term of this patent is extended or adjusted under 35 U.S.C. 154(b) by 91 days.

(21) Appl. No.: 10/694,749

(22) Filed: Oct. 29, 2003

(51) Int. Cl.
*A61F 5/00* (2006.01)

(52) U.S. Cl. ............................ 602/26; 602/16; 602/23; 602/62; 602/5

(58) Field of Classification Search ............... 602/5, 602/16, 23, 24–25, 26, 62–63; 2/22, 24
See application file for complete search history.

(56) References Cited

U.S. PATENT DOCUMENTS

| | | | | |
|---|---|---|---|---|
| 183,376 | A * | 10/1876 | Darrach | 602/26 |
| 4,372,298 | A * | 2/1983 | Lerman | 602/26 |
| 4,407,276 | A | 10/1983 | Bledsoe | |
| 4,572,170 | A * | 2/1986 | Cronk et al. | 602/26 |
| 4,607,628 | A * | 8/1986 | Dashefsky | 602/26 |
| 4,781,179 | A * | 11/1988 | Colbert | 602/26 |
| 4,796,610 | A * | 1/1989 | Cromartie | 602/26 |
| 4,982,732 | A * | 1/1991 | Morris | 602/16 |
| 5,085,210 | A * | 2/1992 | Smith, III | 602/26 |
| 5,107,824 | A * | 4/1992 | Rogers et al. | 602/16 |
| 5,116,296 | A * | 5/1992 | Watkins et al. | 482/91 |
| 5,135,469 | A * | 8/1992 | Castillo | 602/16 |
| 5,277,697 | A * | 1/1994 | France et al. | 602/16 |
| 5,286,250 | A * | 2/1994 | Meyers et al. | 602/16 |
| 5,302,169 | A * | 4/1994 | Taylor | 602/16 |
| 5,562,605 | A * | 10/1996 | Taylor | 602/26 |
| 5,586,970 | A * | 12/1996 | Morris et al. | 602/26 |
| 5,599,288 | A * | 2/1997 | Shirley et al. | 602/26 |
| 5,733,321 | A * | 3/1998 | Brink | 607/111 |
| 5,741,220 | A * | 4/1998 | Brink | 602/14 |
| 5,800,491 | A * | 9/1998 | Kolen et al. | 607/108 |
| 5,823,931 | A * | 10/1998 | Gilmour | 602/24 |
| 5,873,847 | A | 2/1999 | Bennett et al. | |
| 6,302,858 | B1 * | 10/2001 | DeToro et al. | 602/5 |
| 6,461,318 | B1 | 10/2002 | Freeman et al. | |
| 6,471,664 | B1 * | 10/2002 | Campbell et al. | 602/16 |
| 6,551,264 | B1 * | 4/2003 | Cawley et al. | 602/16 |
| 6,821,261 | B1 * | 11/2004 | Doty et al. | 602/5 |
| 2004/0054307 | A1 * | 3/2004 | Mason et al. | 602/16 |

OTHER PUBLICATIONS

AliMed Printout, Canadian Knee Orthosis, Printed Jun. 1, 2005, one page.*

* cited by examiner

*Primary Examiner*—Henry Bennett
*Assistant Examiner*—Amanda Wieker
(74) *Attorney, Agent, or Firm*—Harpman & Harpman

(57) ABSTRACT

An adjustable knee brace for immobilization of a patient's knee in multiple adjustment angular inclinations for use in therapeutic applications. The knee brace has a sheet of cushion material which is adapted to be wrapped about and secured to the patient's leg by a pair of interconnected rigid upper and lower leg engagement plates and associated straps. The leg engagement plates are determined to be registerably engaged against the medial aspect of the leg above and below the knee and have an adjustable articulated locking interconnecting hinge assembly extending there between. An independent knee engagement pad provides knee stabilization in cooperation with leg engagement plates.

10 Claims, 9 Drawing Sheets

KNEE BRACE IMMOBILIZER

BACKGROUND OF THE INVENTION

1. Technical Field

This invention relates to knee braces more particularly to a securing apparatus to immobilize the knee joint of a human. In therapeutic treatment of the knee which includes surgery and joint replacement it is often required to stabilize the knee there after to unload the effective ligaments to impart medial and lateral stability to the knee for a precise period of time for healing.

2. Description of Prior Art

Prior art devices of this type have been used to stabilize and immobilize the knee are directed to a variety of knee brace configurations which are secured to the leg above and below the knee with a mechanical support linkage there between, see for example U.S. Pat. Nos. 4,407,276, 5,135,469, 5,823,931, 5,873,847, 6,461,318.

An articulated knee brace is illustrated in U.S. Pat. No. 4,407,276 illustrating an upper and lower leg engagement cuff with bi-lateral interconnecting elastic strap and a knee pad extending over the expose knee cup.

U.S. Pat. No. 5,135,469 is directed to a post surgical knee brace which incrementally is adjustable. The brace has pairs of upper and lower struts interconnected by a pair of oppositely disposed ratio-swing hinges which allow for incremental angularly bi-lateral adjustments.

A knee brace is described in U.S. Pat. No. 5,823,931 in which an upper and lower leg engagement arms are secured to the leg above and below the knee. A bisymmetric hinge interconnects the arms and has a pair of attachment levers extending there from, each with its own pivot access in vertically aligned and spaced relation to one another.

U.S. Pat. No. 6,561,318 claims an anatomical brace with rapid release securement members for protecting a uniform pivoting joint is disposed between the respective limb engagement members.

An orthopedic splint can be seen in U.S. Pat. No. 5,873,847 disclosing a pair of end plates interconnected by continuous adjustable straps to limit flexing and extension with a spring to pre-load same.

Exhibit A and B are set forth below illustrating catalog sheets which refer to the prior art disclosure.

Exhibit A is a catalog sheet from Alimed, Inc., page BQ53 illustrates a number of different immobilizer/and stabilization devices for knees having a variety of posterior medial and lateral stops with contoured leg wraps and adjustable bi-lateral hinge assemblies.

Exhibit B is a catalog sheet from PEL illustrating a number of default knee immobilizers utilizing wrap around fabric panels with interdisposed splints and deformable support stays as an example of the currently available immobilizations in the market place.

SUMMARY OF THE INVENTION

An articulated adjustable knee immobilizer brace having a flexible wrap around fabric sheet with selectively attached upper and lower interconnected leg engagement plates. Each of the leg engagement plates has multiple non-elastic adjustable straps extending there from for securing the brace to the patient's leg. An incrementally adjustable locking hinge assembly between the leg engagement plates allows for selective angular leg position adjustment dependent on the therapeutic positions so required. An independent knee engagement restraint is adjustably positioned from the respective leg engagement plates providing additional support to the knee.

DESCRIPTION OF THE PREFERRED EMBODIMENT

Figure 1:
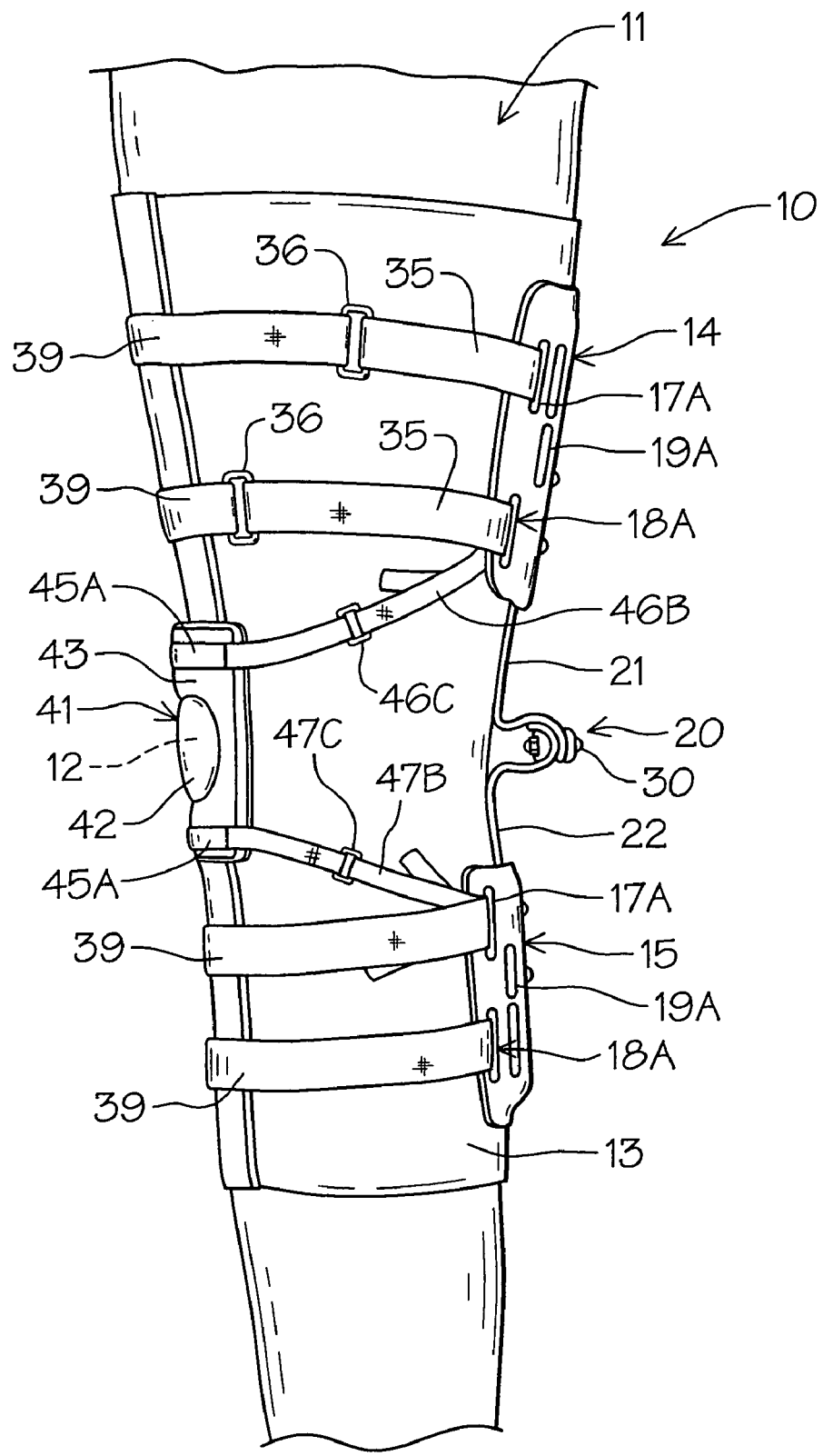
FIG. 1 is a modified side elevational view of the knee brace of the invention on a portion of a patient's leg.
Figure 2:
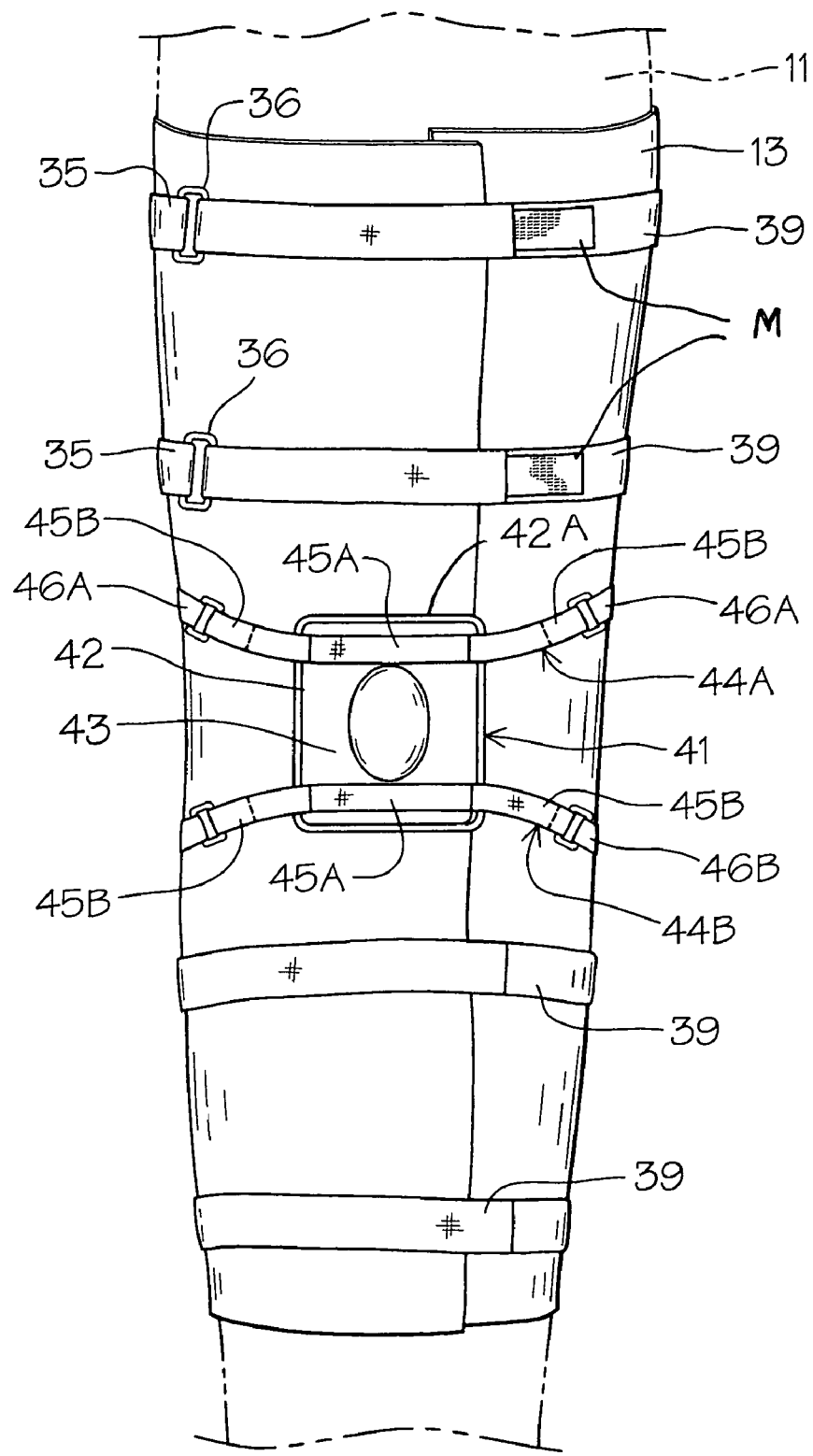
FIG. 2 is a front elevational view thereof.
Figure 3:
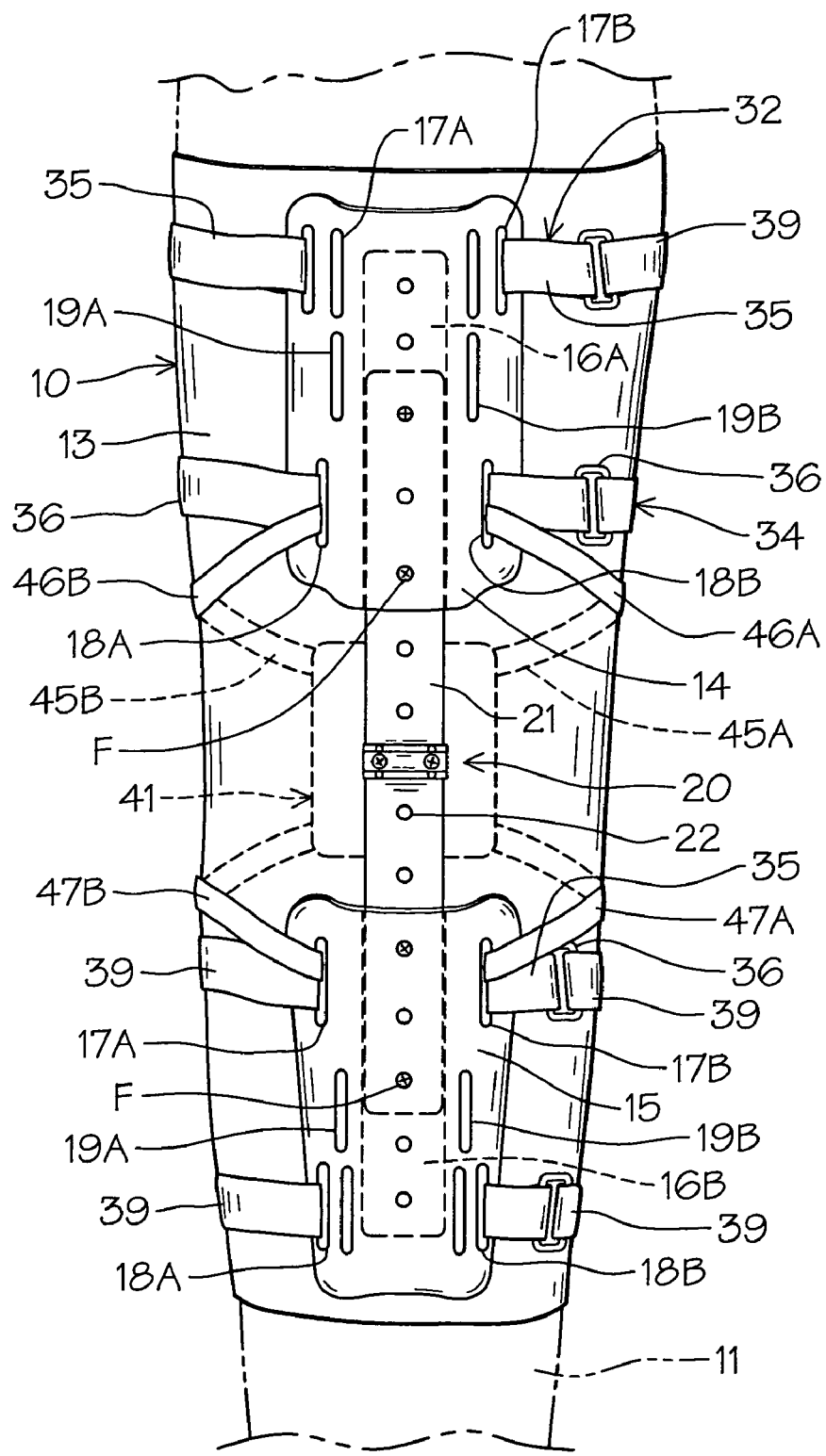
FIG. 3 is a rear elevational view thereof.
Figure 8:
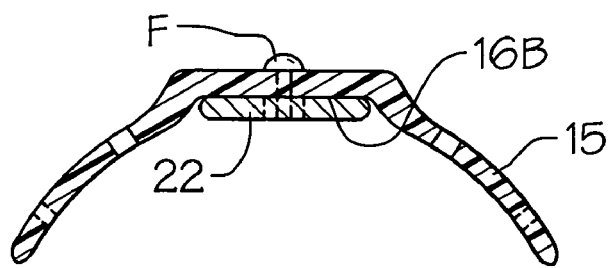
FIG. 8 is a cross-sectional view on lines 8—8 of FIG. 5.
Figure 9:
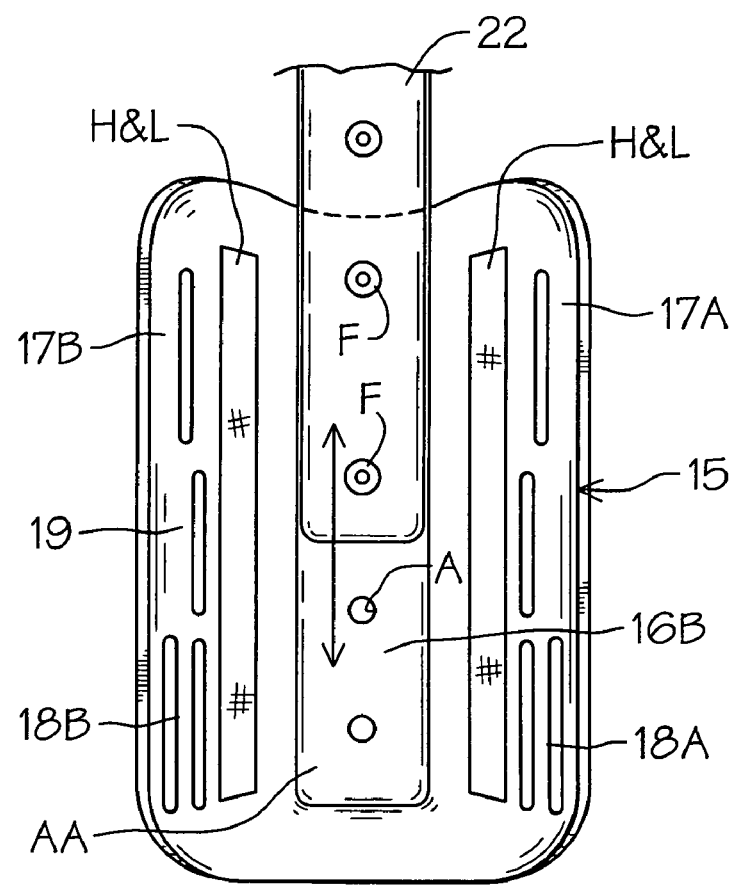
FIG. 9 is rear elevational view of the leg engagement plate illustrated in FIG. 6 of the drawings.

Referring to FIGS. 1–3 of the drawings, a knee immobilization brace 10 can be seen positioned over a portion of a patient's leg 11 and knee 12. The brace 10 has a flexible sheath 13 of cushion material disposed to be wrapped around the patient's leg 11 extending above and below the knee. Attached to the flexible sheath 13 by inter-engaging interlocking hook and loop material M is a pair of interconnected contoured leg engagement plates 14 and 15 which are vertically aligned in spaced relation to one another. Each of the leg engagement plates 14 and 15 are generally of a rectangular configuration having a central longitudinally extending recessed channel portions 16A and 16B respectively therein, as best seen in FIGS. 3, 4 and 8 of the drawings.

A plurality of strap mounting slots can be seen at 17A and 17B formed within the respective leg engagement plates 14 and 15 in oppositely disposed relation to one another on either side of the respective channel areas 16A and 16B, best illustrated in FIG. 3 of the drawings. The respective slots 17A and 17B orientation is such that a variety of different strap mounting positions on the leg engagement plates 14 and 15 can be achieved with adjacent parallel slot pairs 18A and 18B and 19A and 19B in horizontally spaced relation thereto on respective leg engagement plates 14 and 15.

Figure 4:
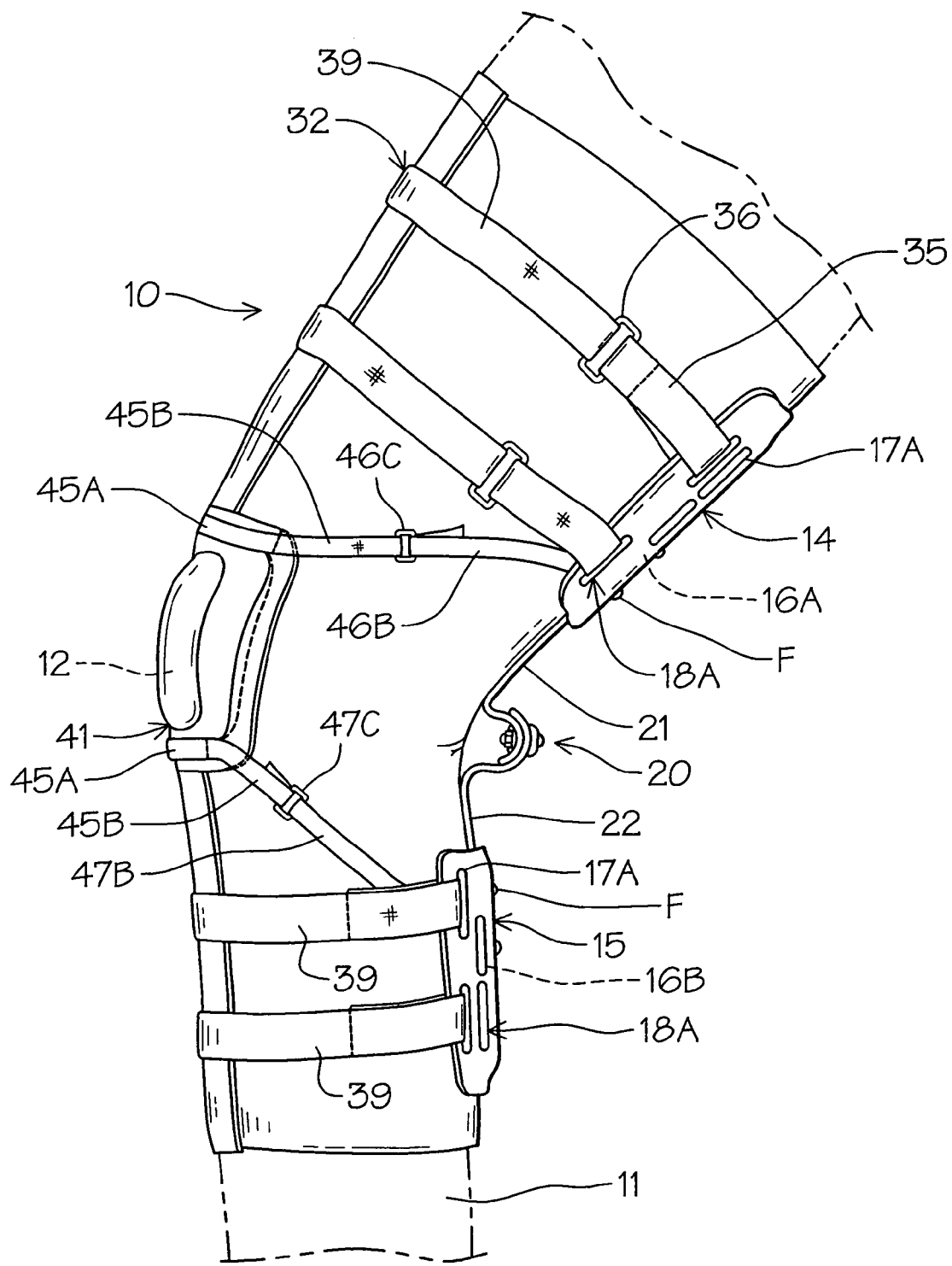
FIG. 4 is a side elevational view of the knee brace of the invention on a portion of a patient's leg in angular adjusted position illustrating the range of adjustment.
Figure 6:
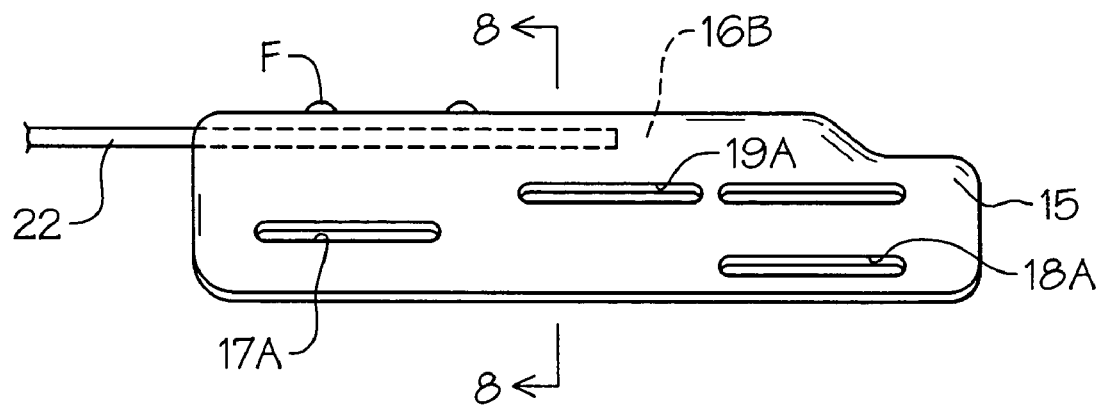
FIG. 6 is a partial side elevational view of a leg engagement plate and hinge engagement extension of the invention.
Figure 7:
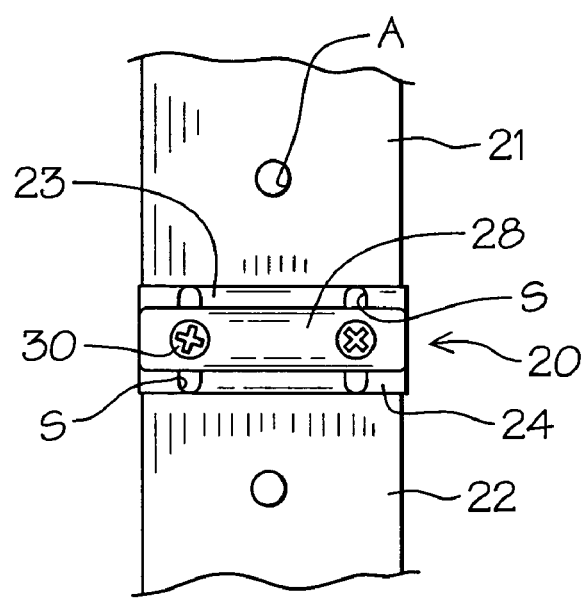
FIG. 7 is an enlarged partial rear elevational view of the hinge assembly.

The leg engagement plates 14 and 15 are transversely contoured to conform with the posterior medial leg portion with engagement above and below the knee 12 as best seen in FIGS. 4, 6 and 7 of the drawings.

Figure 10:
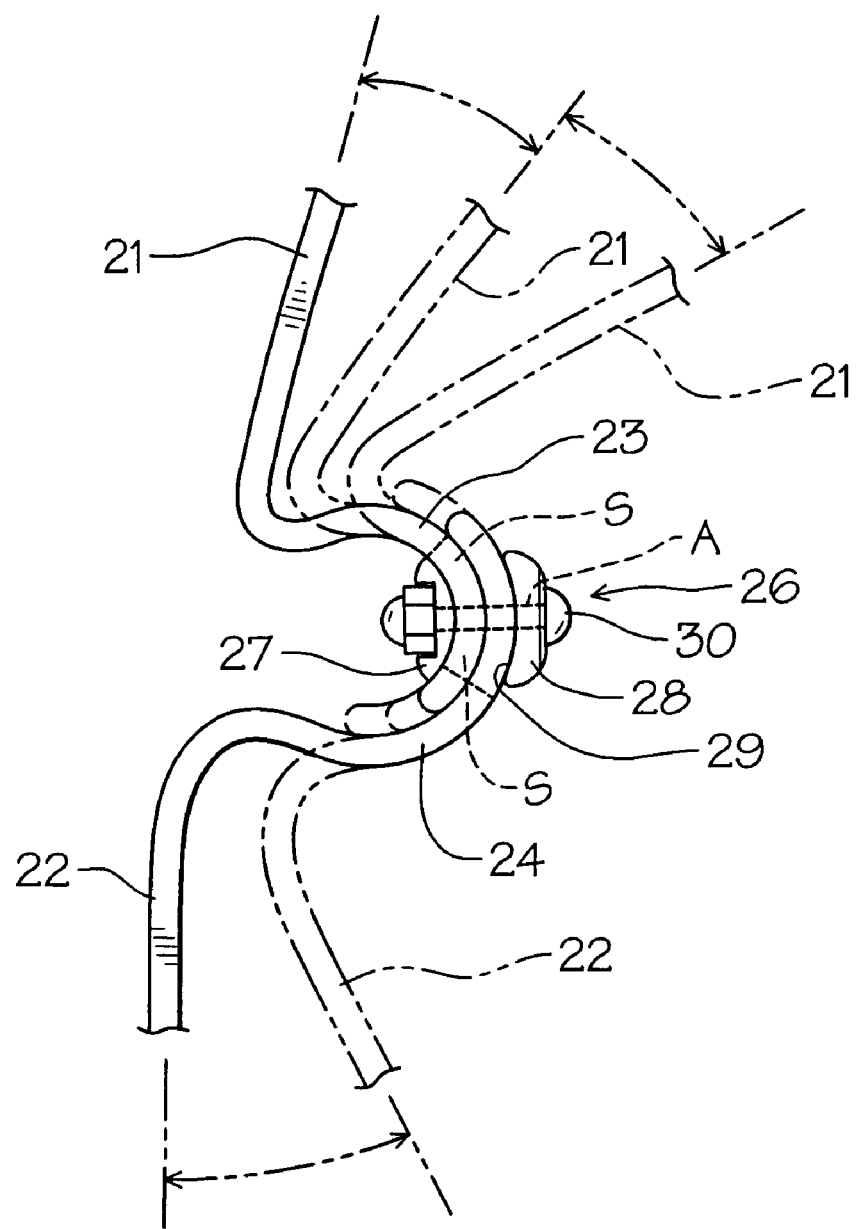
FIG. 10 is an enlarged side elevational view of the hinge assembly of the invention.

Referring now to FIGS. 3, 4 and 10 of the drawings, an adjustable hinge assembly 20 can be seen having an upper leg element 21 and a lower leg element 22 extending there from, both comprised of metal alloys or other suitable material. The upper leg element 21 is adjustably secured within the recess channel 16A of the upper leg engagement plate 14 by multiple fasteners F as will be described in detail hereinafter, with an articulated curved free end at 23. The lower leg element 22 is correspondingly secured within the recess channel 16B of the lower leg engagement plate 15 by fasteners F and also has an articulated curved free end at 24.

The articulated curved free ends 24 and 25 of the respective upper and lower leg elements 21 and 22 have spaced parallel adjustment slots S within that overlie one another when so engaged for aligned registration as seen in FIG. 10 of the drawings.

The hinge assembly 20 is formed by the overlapping respective articulated ends 24 and 25 with a hinge block 27 registerably positioned within the articulated free end 23 of the upper leg element 21 and a compression cap fitting 28 having a curved intermediate surface 29 is positioned over the alignment slots S in the articulated free end 24 of the lower leg element 22 in oppositely disposed aligned relation to the hinge block 27. The compression cap 28 and hinge block 27 are registerably secured together by a pair of threaded fastener assemblies 30 extending through respective aligned apertures A therein and the corresponding slots S of the respective upper and lower leg elements 21 and 22 as hereinbefore described.

An effective range of motion of the upper leg element 21 to the lower leg element 22 is indicated generally in broken lines 21 and 22 in FIG. 10 of the drawings. An example of such application of range of motion there between can be seen in FIG. 4 of the drawings in which the lower leg element 22 has been displaced into a corresponding angular relationship with the upper leg element 22 and associated upper and lower leg engagement plates 14 and 15 secured to the patient's leg 11.

It will be seen that by incremental adjustment of the hinge 20, a variety of different angular inclinations can be achieved within the scope and range as described above.

Figure 5:
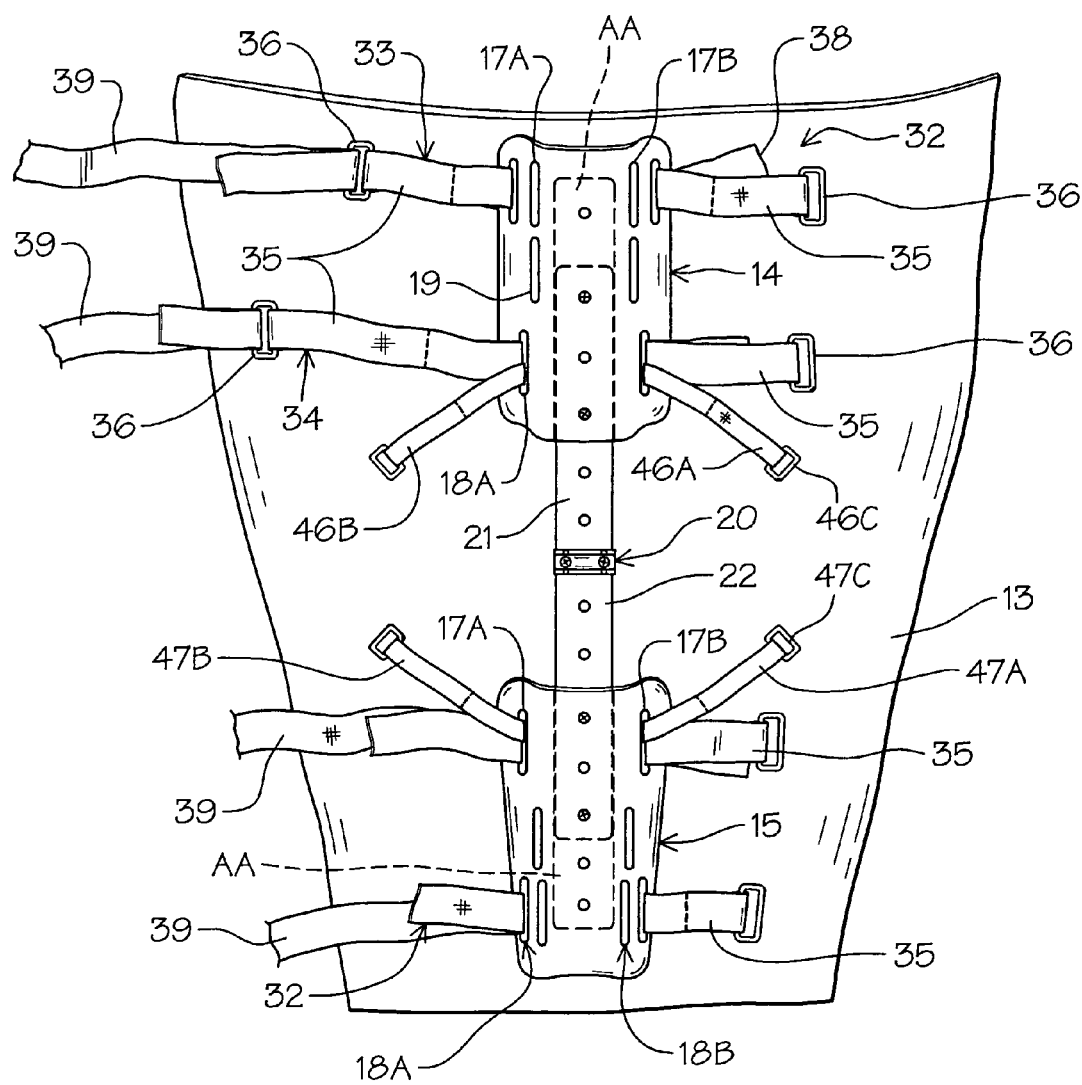
FIG. 5 is a rear elevational view of the knee brace of the invention before placement around a patient's leg.
Figure 11:
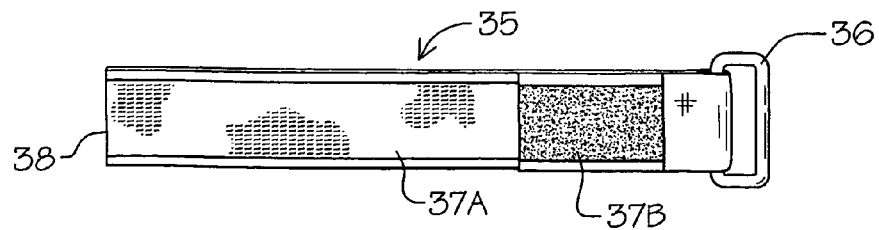
FIG. 11 is a side elevational view of a leg attachment strap.

Referring now to FIGS. 2, 3 and 5 of the drawings, a plurality of securing straps generally indicated at 32 can be seen with the upper leg engagement plate 14 having pairs of adjustable straps 33 and 34 extending from the respective oppositely disposed strap slots 17A and 17B and 18A and 18B. Each of the strap pairs 33 and 34 has an attachment strap 35 with a buckle fitting 36 on one end and a hook and loop fabric fastener portions 37A and 37B on one side of the oppositely disposed end as seen in FIG. 11 of the drawings. The straps 35 free end at 38 are looped through the respective strap slots in the upper leg engagement plate 14 and secured to itself by engagement of the hook and loop material 37A and 37B.

Figure 12:
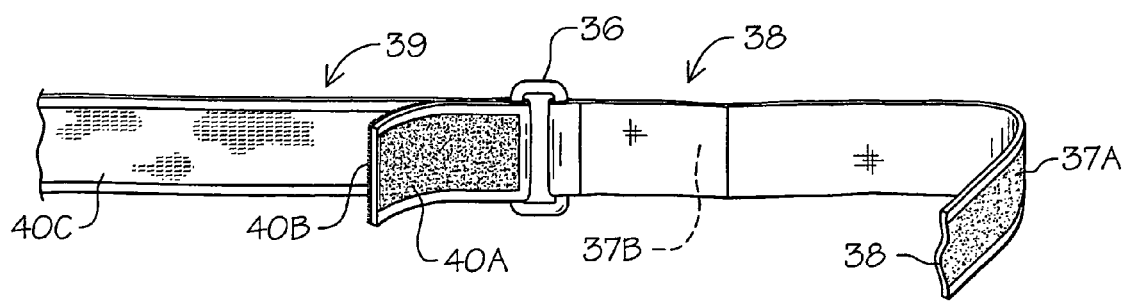
FIG. 12 is a modified side elevational view of a leg attachment strap extension interengaged on the strap shown in FIG. 11.

An extension attachment strap 39 as seen in FIG. 12 of the drawings has oppositely disposed hook fabric surfaces 40A and 40B extending inwardly from one end and a loop fabric surface 40C extending the remaining length of the strap. This arrangement of hook and loop fabric material will allow for the strap 39 to be looped through the corresponding buckle fitting 36 of the respective attachment straps 35 and extend around the patient's leg 11 and looped through oppositely disposed buckle fitting 36 of the corresponding strap 35 extending from the opposite attachment slot 17B securing the upper leg engagement plate 14 to the patient's leg 11 as best illustrated in FIGS. 2 and 5 of the drawings. A corresponding strap arrangement of straps 39 and 35 extend from respective slots 18A and 18B, the lower leg engagement plate 15 has an attachment strap 35 extending from perspective slots 17B and 18B and extension attachment straps 39 extending directly from respective slots 17A and 18A for inter-engagement about the patient's leg 11.

Referring now to FIGS. 1 and 2 of the drawings, a knee support pad 41 can be seen having a generally flat rectangular body member 42 of a soft cushion material with an apertured reinforcement element 43 secured on the front side thereof inwardly of the perimeter edge 42A of the body member 42. A pair of positioning and retaining straps 44A and 44B are secured across the respective upper and lower surfaces thereof. Each of the retaining straps 44A and 44B are made up of interconnected strips of hook 45A and loop 45B material as previously described and best seen in FIG. 2 of the drawings.

The knee support pad 41 and integral reinforcement element 43 as hereinbefore described provides direct support for the patient's knee 12 and is fully adjustable to accommodate and comply to the prescribed angular inclination imparted by the adjustable hinge assembly 20 as hereinbefore disclosed.

In use, the knee brace immobilizer 10 of the invention is positioned about a patient's leg 11 with the hinge assembly 20 being directly behind the patient's knee 12. The flexible sheath 13 with attached upper and lower leg engagement plates 14 and 15 is wrapped around the leg 11 in overlapping relation and secured by the multiple securing straps 32 which adjustably extend from the respective leg engagement plates 14 and 15. The adjustable hinge assembly 20 is secured to hold the leg in prescribed angular inclination by loosening and tightening of the fasteners 30 on the compression cap 28 as previously described.

The knee pad 41 is positioned over the knee 12 centrally thereon by apertured reinforcement element 43 and with its retaining straps 45A and 45B and 46A and 46B are adjusted to secure the knee pad 41 in place as hereinbefore described.

Referring back to FIGS. 5 and 6 of the drawings, it will be seen that each of the respective leg engagement plates 14 and 15 can be selectively adjusted in distance from the respective hinge assembly 20's upper and lower leg elements 21 and 22 by longitudinal repositioning with the respective slots 16A and 16B and therefore each other through the plurality of mounting apertures A within extending in longitudinally spaced relation to one another therein. Correspondingly, the upper and lower leg engagement plates 14 and 15 have aligned plate apertures A therein which allow for selective repositioning and securing again by the fasteners F of the respective leg elements 21 and 22 therewith as indicated by adjustment areas AA in FIG. 5 of the drawings. This will allow the leg engagement plates 14 and 15 and associated hinge assembly 20 to be used on a variety of different patients within the longitudinal adjustment parameters so describes thus making the immobilization brace 10 of the invention applicable to a variety of different in size individuals legs by simple adjustment of the overall length by the repositioning of the respective upper and lower leg elements 21 and 22 within the corresponding channels 16A and 16B as noted.

It will thus be seen that a new and novel knee immobilization brace of the invention has been illustrated and described and that various changes and modifications may be made thereto without departing from the spirit of the invention.

We claim:

1. An adjustable therapeutic knee immobilization brace for controlling the degree of motion to a person's knee comprising;

a flexible sheet of cushion material adapted to wrap around a wearer's leg extending above, below and encompassing the wearer's knee, rigid upper and lower leg engagement plates adapted to be fitted against the posterior face of the leg above and below the knee, an adjustable locking hinge assembly extending between and interconnecting said upper and lower leg engagement plates on the posterior face of said leg in oppositely disposed relation to said knee, adjustably secured thereto by retaining straps extending from respective upper and lower engagement plates, and means for adjustably securing said knee immobilization brace to the wearer's leg.

2. The adjustable knee brace set forth in claim 1 wherein said rigid upper and lower leg engagement plates are selectively secured to a non-leg engagement surface of said sheet of cushion material.

3. The adjustable knee brace set forth in claim 1 wherein said adjustable locking hinge assembly comprises, an upper and lower leg element extending from said respective leg engagement plates, a free end of said upper leg element adjustably engaged with a free end of said lower leg element, wherein said engagement ends have C-shaped overlapping end portions with an adjustable apertured locking assembly thereon.

4. The adjustable knee brace set forth in claim 3 wherein said apertured locking assembly comprises, an apertured hinge block and an apertured compression cap in aligned relationship to one another, fasteners extending through said apertures thereof and through an elongated opening in each of said C-shaped overlapping end portions.

5. The adjustable knee brace set forth in claim 1 wherein said means for adjustably securing said knee immobilization brace to the wearer's leg comprises, a plurality of non-elastic straps adjustably extending from multiple strap mounting slots in said respective upper and lower leg engagement portions and strap to strap interengagement means thereon.

6. The knee brace set forth in claim 5 wherein said strap to strap interengagement means comprises hook and loop material positioned respectively thereon.

7. The knee brace set forth in claim 5 wherein said strap mounting slots further comprise, oppositely disposed pairs of parallel spaced slots in longitudinally spaced relation on said respective upper and lower leg engagement plates.

8. The adjustable knee brace set forth in claim 1 wherein said upper and lower leg engagement plates are transversely adapted to engage the wearer's leg, and a mounting channel defined in each of said upper and lower leg engagement plates.

9. The knee brace set forth in claim 6 wherein said adjustable hinge assembly further comprises, selectively aligned apertures in upper and lower leg elements and said respective mounting channels with registerable fasteners there through for longitudinal repositioning of said respective leg elements in said mounting channels in relation to said respective upper and lower leg engagement plates and to one another.

10. The adjustable knee brace set forth in claim 1 wherein said knee stabilization means comprises a knee support pad adapted to overlie the wearer's knee, an apertured reinforcement element secured on said knee support pad in spaced relation to the perimeter edge thereof, said reinforcement element defining a knee alignment area therewithin and, positioning retaining straps extending from said knee support pad to said respective upper and lower leg engagement plates.

\* \* \* \* \*